United States Patent [19]

Mark

[11] 4,353,830

[45] Oct. 12, 1982

[54] PROCESS FOR THE PREPARATION OF SUBSTITUTED AMIDINES

[75] Inventor: Victor Mark, Evansville, Ind.

[73] Assignee: General Electric Company, Mt. Vernon, Ind.

[21] Appl. No.: 106,678

[22] Filed: Dec. 26, 1979

[51] Int. Cl.$^3$ .................. C07D 207/04; C07C 81/00
[52] U.S. Cl. ......................... 260/326.86; 260/501.1; 260/501.14; 260/239 A; 260/239 R; 260/239.3 R
[58] Field of Search ................. 260/326.86, 501.14, 260/501.1

[56] References Cited

PUBLICATIONS

Eilingsfeld et al., Angew. Chem., vol. 72, (1960), pp. 836–845, 893.

*Primary Examiner*—David B. Springer
*Attorney, Agent, or Firm*—Martin B. Barancik; William F. Mufatti

[57] ABSTRACT

Amidines are one of the strongest organic bases and find application where this property is needed, such as in phase transfer catalysis, in the form of their substituted derivatives. Their use, however, has been hampered by their expensive nature due to the only mediocre yields in their preparation. The present invention provides a process for the preparation of substituted amidines in essentially quantitative yields.

10 Claims, No Drawings

PROCESS FOR THE PREPARATION OF SUBSTITUTED AMIDINES

Amidines are one of the strongest organic bases and find application where this property is needed, such as in phase transfer catalysis, in the form of their substituted derivatives. Their use, however, has been hampered by their expensive nature due to the only mediocre yields in their preparation. The present invention provides a process for the preparation of substituted amidines in essentially quantitative yields.

BACKGROUND OF THE INVENTION

The most general, and economical, method for preparing substituted amidines (B), (B') and (B'') is from
(a) chloro(methylenammonium) chlorides (also called chloroformiminium chlorides), represented by formulae (A), (A'), and (A''), with primary amines

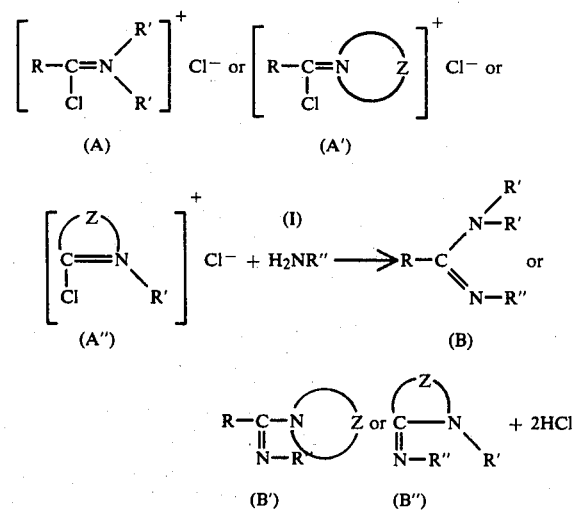

and,
(b) substituted imidoyl chlorides (C) with secondary or primary amines

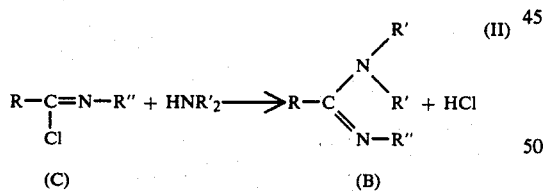

wherein R is a monovalent substituent selected from the group consisting of hydrogen, alkyl, aryl, aralkyl, alkaryl, cycloalkyl, alkenyl, cycloalkenyl and heterocyclic radicals; R' and R'' are monovalent organic radicals independently selected from the group consisting of alkyl, aryl, aralkyl, alkaryl, cycloalkyl, alkenyl, cycloalkenyl and heterocyclic radicals; and, Z is a divalent organic radical completing a 4 to 8 membered cycloaliphatic ring and containing (i) from 2 to 6 carbon atoms or (ii) from 2 to 6 carbon atoms and one hetero atom selected from the group consisting of oxygen, sulfur, and nitrogen with the proviso that no hetero atom is adjacent said nitrogen atom.

These processes are illustrated (a) in the book by P.A.S. Smith, *Open Chain Nitrogen Compounds*, Vol. 1, pp. 177-184 (1965), W. A. Benjamin, Inc., New York; (b) in the review article by R. L. Schriner and F. W. Neumann, in *Chemical Reviews*, Vol. 35, pp. 351-425 (1944); and in individual articles, such as (c) *Chemistry and Industry*, 1971, p. 175; and (d) *Angewandte Chemie*, Vol. 72, pp. 836-845 (1960). The yields, however, are only mediocre, usually between 40 and 70%, and drastic heating conditions (between 150° and 180° C.) are required to effect reactions with the more basic amines (as shown in reference (d), p. 839).

SUMMARY OF THE INVENTION

It has now been found that reactions I and II can be made facile and essentially quantitative by adding together with the primary or secondary amines one of the following coreactants:

(a) at least one, but preferably two, moles of a tertiary amine of high basicity;

(b) at least one, but preferably two, moles of a strong inorganic base;

(c) at least one, but preferably two, additional moles of the primary or secondary amine reactant;

(d) at least one, but preferably two, moles of the amidine product formed in the reaction.

The role of the strong base in reactions I and II is not only to liberate the amine reactant that is partially inactivated by being tied up as its hydrochloride, but to participate actively in the reaction, which is shown in its simplified form by equations I and II. Actually, there are reaction intermediates (D), (E) and (F) which are produced between the reactants and the amidine products:

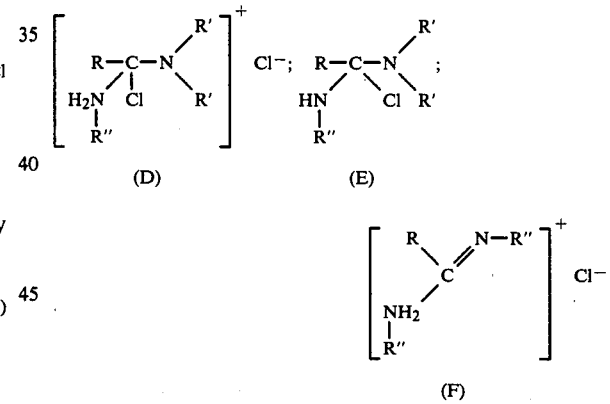

wherein R, R' and R'' are as defined above. The added organic or inorganic base facilitates the conversion of these intermediates to (B), thus not only increasing the yield, but the reaction rate as well. Therefore, the high reaction temperatures (150° to 180° C.) previously necessary for the reaction of the halides with strongly basic amines when used in the stoichiometrically required amounts (ref. (d)) are no longer needed and the reaction can, in fact, proceed exothermally in the presence of the added organic or inorganic base.

Examples of the strong inorganic bases which can be employed are alkali or alkaline earth metal hydroxides, such as sodium hydroxide, potassium hydroxide, calcium hydroxide, and the like.

Strong organic bases which can be employed are tertiary aliphatic and cycloaliphatic amines, dialkyl amines, di- or poly (tertiary) amines, and the like. Examples include triethyl amine, tripropyl amine, tributyl amine, dicyclohexylmethyl amine, diisopropylamine, quinuclidine, hexamethylenetetramine, and the like.

In one preferred embodiment, the extra organic base is the primary amine itself ($H_2NR''$) of equation I or the secondary amine, $HNR'_2$, of equation II. Examples of the primary amine include methylamine, ethylamine, propylamine, isopropylamine, tert-butylamine, octadecylamine, aniline, p-chloroaniline, 4-aminopyridine, ethanolamine, 2-methoxyethylamine and similar substituted aliphatic, cycloaliphatic, aromatic and heterocyclic amines. Examples of the secondary amines which can be employed include dimethylamine, diethylamine, diisopropylamine, methylbutylamine, ethylcyclohexylamine, pyrolidine, piperidine, morpholine, N-methylaniline, diethanolamine, and the like.

In another preferred embodiment, the extra organic base is the amidine itself, that is, the reaction product of equations I and II. This is particularly preferred since amidines are more powerful bases than any of the tertiary amines or the primary amines required in equation II or the secondary amines of equation II and are thus capable to effect quantitative conversions. Furthermore, the reactions are especially clean, since there are no extraneous products formed and there is, thus, no need for extra separation steps, such as distillation. The amidine tied up in the reaction as its hydrochloride can be set free at the end of the reaction by concentrated aqueous sodium hydroxide solution and reused anew.

The halide precursors of reactions I and II are best prepared by the reaction of the appropriate carboxylic acid amide with phosgene as represented by III and IV:

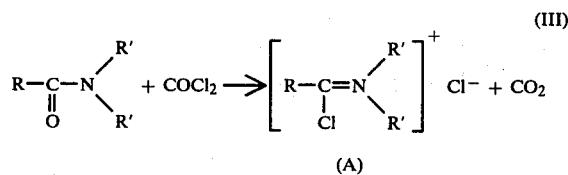

(A)

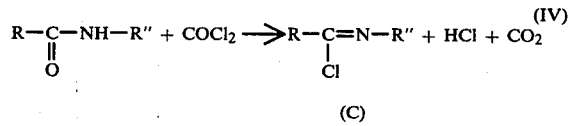

(C)

wherein R, R' and R'' are as defined above.

Preparative methods for (A) and (C) are given in references (a), pp. 147–148, 177–184 and 272; (d) and in (e) *Chemische Berichte*, Vol. 95, pp. 126–135 (1962).

The preparation of amidines is best carried out without the isolation of (A) and (C) which are moisture sensitive. Instead, reactions III and I, and IV and II, are combined and carried out in the same reactor, with complete exclusion of moisture, to secure maximum, often quantitative yields. It is, therefore, best to introduce phosgene into a solution or slurry of the carboxylic acid amide in an inert liquid until the reaction is complete, as evidenced by the cessation of $CO_2$ evolution. The system is dephosgenated (by inert gas purge or applications of vacuum) and the amine reactant is introduced in excess or in the presence of the tertiary amine or amidine. The reaction is facile and usually exothermic. Internal (such as by the refluxing solvent) or external cooling is applied to maintain the reaction temperature at optimum levels, which is between 0° and 100° C., preferably 30° and 50° C. When inorganic bases are used, they are best introduced after the theoretical amount of primary amine has been added. Preferably, the addition of the inorganic base is gradual so as to minimize the hydrolysis of (A) and (C) to the amides. It is also best to use relatively concentrated (40–50%) solutions of sodium or potassium hydroxide or slurries of calcium hydroxide or barium hydroxide. If the amidine formed is liquid, it is best separated from the aqueous brine by phase separation. If solid, it is best filtered off, washed and dried.

DETAILED DESCRIPTION OF THE INVENTION

The invention will become more clear when considered in light of the following examples which set forth the best mode presently known for carrying out the inventive process.

EXAMPLE 1

(α-Chlorobenzylidene)dimethylammonium chloride

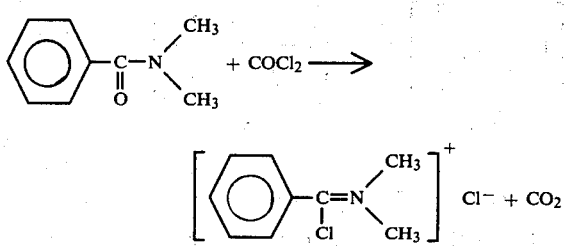

This example illustrates the preparation of the titled compound by adaptation of the conventional methods disclosed in the above-identified references.

A solution of 74.6 g (0.5 mole) of N,N-dimethylbenzamide (m.p. 43°–44° C.), in 250 ml of methylene chloride was charged to a one-liter, four-necked flask equipped with a mechanical stirrer, a thermometer reaching into the liquid, a gas inlet tube reaching below the level of the solution and a dry ice condenser whose exit line was connected to a caustic scrubber via a bubbler. Pure phosgene gas was introduced into the flask with good agitation at a rate of ca. 0.5 g/min. The formation of titled product was indicated by a mild exotherm, which reached its peak of 33° C. in ca. 10–15 min. and by the steady evolution of $CO_2$ which was indicated by the bubbler. After ca. 110 minutes (corresponding to a 10% excess) the phosgene stream was turned off and heating to reflux was started. After 15–20 minutes, the heat was turned off, the dry ice condenser was replaced by a cold water condenser and the excess phosgene was boiled off. Care should be taken to keep the product (which is a crystalline, moisture sensitive solid, m.p. 91°–94° C.) in solution by replacing the evaporated solvent and by adequate heating. The solution was considered to be phosgene free when the phosgene indicator paper, held in the vapor phase, remained essentially colorless, and this solution was used directly in the next Example 2.

EXAMPLE 2

N'-Cyclohexyl-N,N-dimethylbenzamidine

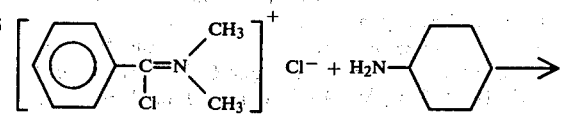

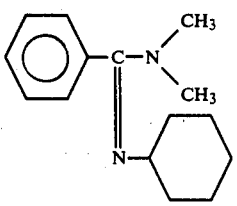

This example illustrates the preparation of the novel N'-cyclohexyl-N,N-dimethylbenzamidine (CDMB) by a conventional method known in the prior art, such as shown in references (a), (b) and (d) above.

To the solution of (α-chlorobenzylidene)dimethylammonium chloride in methylenechloride described in Example 1, there was added dropwise, a solution of 49.6 g (0.5 mole) of cyclohexylamine in 100 ml of methylenechloride. The temperature of the ensuing exothermal reaction rose from 24.5° to 42.5° C. thus keeping the solvent in reflux. After the reaction subsided, the reaction mixture, consisting of a slurry of white solids in a pale yellow solution, was heated to reflux with stirring. After standing overnight, the slurry was filtered, and the solution was stripped of the solvent and the oily residue distilled. The novel amidine (also called N'-cyclohexyl-N,N-dimethylbenzenecarboximidamide) was obtained as a colorless oil, boiling between 78° and 79° C. at 0.04 mm of mercury pressure and having a refractive index of $n_D 21.6$, 1.5400, in 56.0 g corresponding to a 49% yield. Proton nmr infrared and elemental analysis confirmed its proposed structure.

EXAMPLE 3

This examples illustrates one of the invention processes for the preparation of the CDMB of Example 2 in the presence of a strong organic base: triethylamine.

The procedure of Example 2 was exactly repeated, except that the cyclohexylamine was added in form of its solution in 101.2 g (1.0 mole) of triethylamine and, at the end of the reaction, aqueous sodium hydroxide solution (30%) was added to allow the dissolution and decomposition of the triethylamine hydrochloride precipitate in the aqueous phase. The methylenechloride solution was washed with water, separated, dried and the solvent stripped off. The residual oil, identified as pure CDMB, weight 111.9 g and was thus obtained in 97% yield.

EXAMPLE 4

This example illustrates the preparation of CDMB in the presence of CDMB following the process of the invention.

The procedure of Example 2 was exactly repeated, except that a solution of 0.5 mole of cyclohexylamine in 100 ml of N'-cyclohexyl-N,N-dimethylbenzamidine was used. Workup of the reaction as done previously yielded 114.0 g of an oil, shown to be pure CDMB. The yield, accordingly, was 99%.

EXAMPLE 5

This example illustrates another embodiment of the invention process wherein the CDMB was prepared in the presence of an additional mole of the amine reactant.

The procedure of Example 2 was repeated except that utilizing 1.0 mole (99.2 g) of cyclohexylamine yielded 109.0 g or 95% of CDMB instead of 49%.

EXAMPLE 6

(α-Chloroethylidene)dimethylammonium chloride)

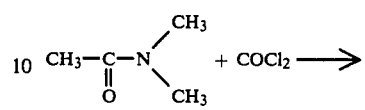

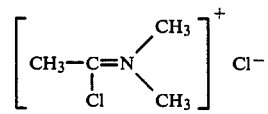

The titled intermediate compound was prepared following the conventional methods disclosed in the above-identified references.

The procedure of Example 1 was repeated, except that 43.5 g (0.5 mole) of N,N-dimethylacetamide was substituted for dimethylbenzamide. The resultant yellowish crystalline slurry was not isolated, but was directly used in the preparation of the amidine of Example 7 below.

EXAMPLE 7

N,N-Dimethyl-N'-phenylacetamidine (DMPA)

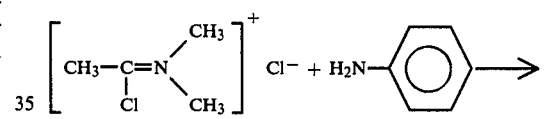

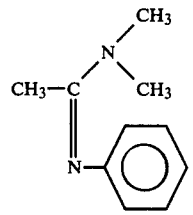

The titled compound was prepared following an adaptation of the conventional methods disclosed in the above-identified references.

To the slurry of the halide (prepared in Example 6) there was added, dropwise, 46.5 g (0.5 mole) of aniline while keeping the temperature below 40° C. with tap water cooling. After the addition was complete, the reaction mixture was heated to reflux for 0.5 hour. Workup of the reaction mixture by washing with water three times, separation and drying with silica gel, followed by stripping of the solvent yielded an oil (66.8 g) which, after distillation in vacuum through a 12-inch column filled with glass halides, yielded the titled amidine (DMPA) in the form of a colorless oil, boiling at 73° C. at 0.12 mm mercury, $n_D$ 19.6, 1.5733 in 21.0 g corresponding to a 26% yield.

EXAMPLE 8

This example illustrates the preparation of DMPA by the method of the invention wherein a strong inorganic base was employed.

The procedure of Example 7 was repeated, except that the addition of the aniline was followed by the addition of 50.0 g (1.2 moles) of sodium hydroxide in the form of a 48% aqueous solution. The yield of distilled DMPA was 64.1 g or 79% of the theoretical.

EXAMPLE 9

α-Chloro-N-methylpyrrolinium chloride

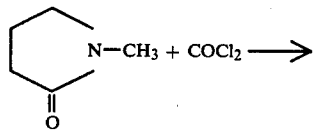

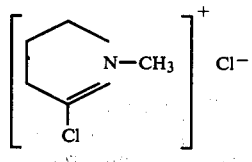

The procedure of Example 1 was repeated, except that 1-methyl-2-pyrrolidinone (49.6 g; 0.5 mole) was substituted for dimethylbenzamide. The cyclic halide (m.p. 76°–78° C.) was not isolated in bulk; instead, the resultant bright yellow solution was used directly for the preparation of the cyclic amidine of Example 10 below.

EXAMPLE 10

Preparation of a cyclic amidine

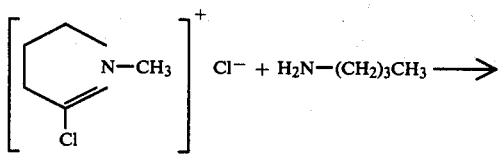

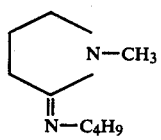

The general procedure outlined in Example 2 was repeated, except that 1.0 mole of n-butylamine was added to the 0.5 mole of cyclic halide prepared in Example 9. The strongly exothermic reaction was moderated by outside cooling. After the reaction subsided, workup was effected as in Example 2. Vacuum distillation produced the novel amidine as a colorless oil, b.p. 30° C. at 0.11 mm mercury pressure, with a refractive index of n_D 22.5, 1.4710. Infrared and proton nuclear magnetic analysis confirmed its structure as illustrated above. The yield was 66.3 g or 86% of the theory.

EXAMPLE 11

Preparation of N-phenylbenzenecarboximidoyl chloride

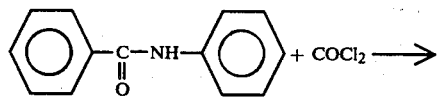

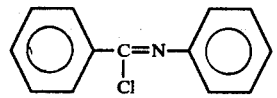

The procedure of Example 1 was repeated with 98.6 g (0.5 mole) of benzanilide in place of the benzamide. The imidoyl chloride was obtained after distillation b.p. 104°–108° C., 1.0 mm mercury, as a low melting solid, m.p. 40°–41° C., and was used in Example 12 below.

EXAMPLE 12

Preparation of N,N'-diphenylbenzamidine

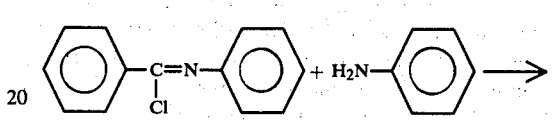

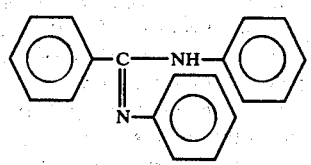

Applying the procedure of Example 7, except for using a mixture of 46.5 g (0.5 mole) of aniline and 52 g (0.5 mole) of triethylamine, a yield of more than 80% of N,N'-diphenylbenzamidine, m.p. 143°–144° C. was obtained. Its hydrochloride melted at 253°–256° C.

EXAMPLE 13

Preparation of (chloromethylene)dimethylammonium chloride

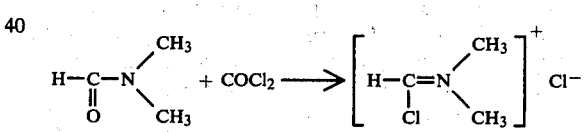

The procedure of Example 1 was repeated except that N,N-dimethylformamide (36.6 g, 0.5 mole) was substituted for the benzamide. The resultant slurry of the chloride (m.p. 140°–144° C.) was used directly, after dephosgenation, in Example 14 below.

EXAMPLE 14

Preparation of N,N-dimethyl-N'-phenylformamidine

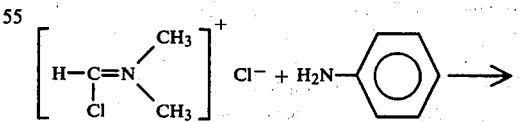

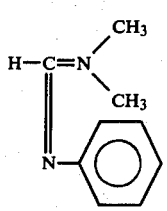

Repeating the procedure of Example 12, but using the halide of Example 13, a high yield (70%) of N,N-dimethyl-N'-phenylformamidine, b.p. 64°-66° C. at 0.04 mm, $n_D$ 22, 1.5926 was obtained. Its hydrochloride had a m.p. of 238°-240° C.

What is claimed is:

1. In process for making substituted amidines which comprises reacting (a) (chloroalkylene)ammonium chlorides with a primary amine or (b) substituted imidoyl chlorides with a secondary or a primary amine the improvement comprising carrying out the reaction in the presence of at least one mole of a coreacted base selected from the group consisting of:
   (A) tertiary amines;
   (B) alkali or alkaline earth metal hydroxide;
   (C) the amidine itself that is the product of the reaction;
   (D) an excess of the primary or secondary amine reactant;
   (E) quaternary ammonium hydroxides, said substituted imidoyl chlorides being represented by the formula

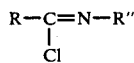

wherein R" is independently selected from the group consisting of $C_1$-$C_{20}$ alkyl, $C_3$-$C_{12}$ cycloalkyl; $C_6$-$C_{14}$ aryl; alkaryl or aralkyl which are combinations of said alkyl and said aryl; substituted alkyl, wherein the substituents are $C_1$-$C_{10}$ alkoxy, $C_1$-$C_{10}$ alkylthio and $C_2$-$C_{12}$ dialkylamino; substituted aryl, wherein the substituents are the same as defined for said substituted alkyl, plus chlorine, bromine and fluorine; and, R is the same as R" or hydrogen; said reaction being conducted in the absence of moisture in an inert medium at temperatures in the range of about 0°-100° C.

2. A process as set forth in claim 1 wherein the (chloroalkylene)ammonium chloride is represented by the following formulae (A), (A') and (A"):

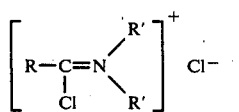

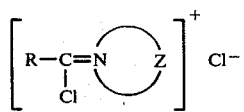

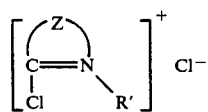

wherein R' is independently selected from the group consisting of $C_1$-$C_{20}$ alkyl, $C_3$-$C_{12}$ cycloalkyl; $C_6$-$C_{14}$ aryl; alkaryl or aralkyl which are combinations of said alkyl and said aryl; substituted alkyl, wherein the substituents are $C_1$-$C_{10}$ alkoxy, $C_1$-$C_{10}$ alkylthio and $C_2$-$C_{12}$ dialkylamino; substituted aryl, wherein the substituents are the same as defined for said substituted alkyl, plus chlorine, bromine and fluorine; R is hydrogen or the same as R'; and, Z is a divalent organic radical completing a 4 to 8 membered cycloaliphatic ring and containing (i) from 2 to 6 carbon atoms or (ii) from 2 to 6 carbon atoms and one hetero atom selected from the group consisting of oxygen, sulfur and nitrogen with the proviso that no hetero atom is adjacent said nitrogen atom.

3. A process as set forth in claim 2 wherein the primary amine is represented by the following formula:

R'—NH₂ wherein R' is as defined in claim 2.

4. A process as set forth in claim 2 wherein the secondary amine is represented by the following formula:

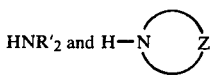

wherein R' and Z are as defined in claim 2.

5. A process as set forth in claim 2 wherein the tertiary amine is selected from the group consisting of trialkylamine, cycloalkyldialkylamine, dicycloalkylalkylamine, tricycloalkylamine, dialkylarylamine, dicycloalkylarylamine and pyridines.

6. A process as set forth in claim 2 wherein the alkali or alkaline earth metal hydroxide is selected from the group consisting of sodium hydroxide, potassium hydroxide and calcium hydroxide.

7. A process as set forth in claim 2 wherein the quaternary ammonium hydroxide is represented by the formula [R₄N]⁺HO⁻ wherein R is as defined in claim 2.

8. A process as set forth in claim 2 wherein the amidine is represented by the general formulae (B), (B') and (B"):

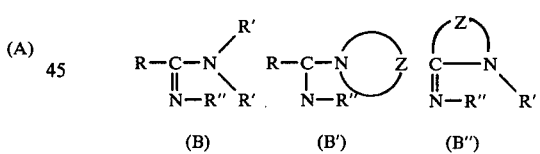

wherein R,R',R" and Z are as defined in claim 2.

9. A process as set forth in claim 2 wherein the primary amine, R"-NH₂ is used in at least one molar excess above the stoichiometric amount.

10. The process as set forth in claim 2 wherein the secondary amine, HNR'₂ and

are independently used in at least one molar excess above the stoichiometric amount.

* * * * *